United States Patent [19]

Wehrmeister

[11] 4,144,766
[45] Mar. 20, 1979

[54] APPARATUS FOR THE IN-SITU DETECTION AND LOCATION OF FLAWS IN WELDS

[75] Inventor: Allen E. Wehrmeister, Lynchburg, Va.

[73] Assignee: The Babcock & Wilcox Company, New York, N.Y.

[21] Appl. No.: 793,026

[22] Filed: May 2, 1977

[51] Int. Cl.² .................................... G01N 29/04
[52] U.S. Cl. ............................... 73/587; 228/104
[58] Field of Search ............ 73/71.4, 88 R, 587; 228/103, 104; 219/109

[56] References Cited

U.S. PATENT DOCUMENTS 3,985,024  10/1976  Horak .................................. 73/71.4
4,033,179  7/1977   Romrell .............................. 73/71.4

OTHER PUBLICATIONS

W. D. Jolly, The Application of Acoustic Emission to In-Process Inspection of Welds, Materials Evaluation, vol. 28, No. 6, Jun., 1970, pp. 135–139.

Primary Examiner—James J. Gill
Attorney, Agent, or Firm—John F. Luhrs; J. M. Maguire

[57] ABSTRACT

Apparatus for the on-line detection and location of weld flaws wherein the acoustic emissions from a fault are segregated from other acoustic emissions by recognizing those emissions from the weld zone falling within a predetermined band of frequencies and locating the fault by determining the time required for the recognized emissions to travel to two spaced apart predetermined points.

7 Claims, 2 Drawing Figures

APPARATUS FOR THE IN-SITU DETECTION AND LOCATION OF FLAWS IN WELDS

This invention relates to the on-line, or in-situ detection, as it may be called, in real time of weld flaws and more particularly to the detection and location of flaws in multiple pass welds as required in joining together thick work pieces such as sections of pressure vessels or pipes. In welding such sections together upwards of seventy five or more weld passes may be required. A well known process used in making such welds is the submerged arc process wherein the arc generated between the welder electrode, or weld wire as it is sometimes called, and the work pieces is submerged in a suitable flux. It will be evident, however, that the invention is equally applicable to other types of welders such as the tungsten inert gas (TIG) type.

It is vital to the integrity of the joined work pieces that the completed weld be free from defects such as caused by slag entrapment or lack of fusion which cannot be visibly detected during the welding process. As a consequence such faults are presently detected by nondestructive, off-line examination techniques only after the weld is complete. It is costly and time consuming to remove faults which such an examination discloses as it may require the removal of several good weld passes before the fault is exposed and repairs can be made.

It is an object of this invention to provide an apparatus whereby a fault may be detected and located upon formation so that the welding process may be then and there interrupted and repairs made in-situ.

It is a further object of this invention to provide such an apparatus utilizing the acoustic emissions from the weld zone traveling through the work piece as a means of detecting flaws.

It is another object of this invention to provide such an apparatus wherein only those acoustic emissions falling within a predetermined band of frequencies are recognized as indicative of a fault.

Still another object of this invention is to provide such an apparatus wherein only those acoustic emissions within the predetermined band of frequencies which originate from within a predetermined distance ahead of and following the welder arc are recognized.

A further object of the invention is to provide an apparatus wherein a plurality of recognized acoustic emissions must be emitted from within a predetermined segment of the weld before recognizing the emissions as indicative of a fault.

A further object of the invention is to provide an apparatus wherein the location of a flaw is determined by measuring the difference in the times required for the recognized emissions to travel to two spaced apart points maintained in fixed spatial relationship to the welder arc.

Still another object of the invention is to provide an apparatus discarding spurious acoustic emissions within the predetermined band of frequencies by recognizing only such emissions as originating between the two spaced apart points.

A further object of the invention is to provide an apparatus wherein formation of a flaw and the location thereof is immediately made known on a suitable readout device and/or by marking the location thereof on the workpiece.

These and other objects will be apparent from the following description taken in connection with the drawings, in which:

DETAILED DESCRIPTION

Figures 1, 2:
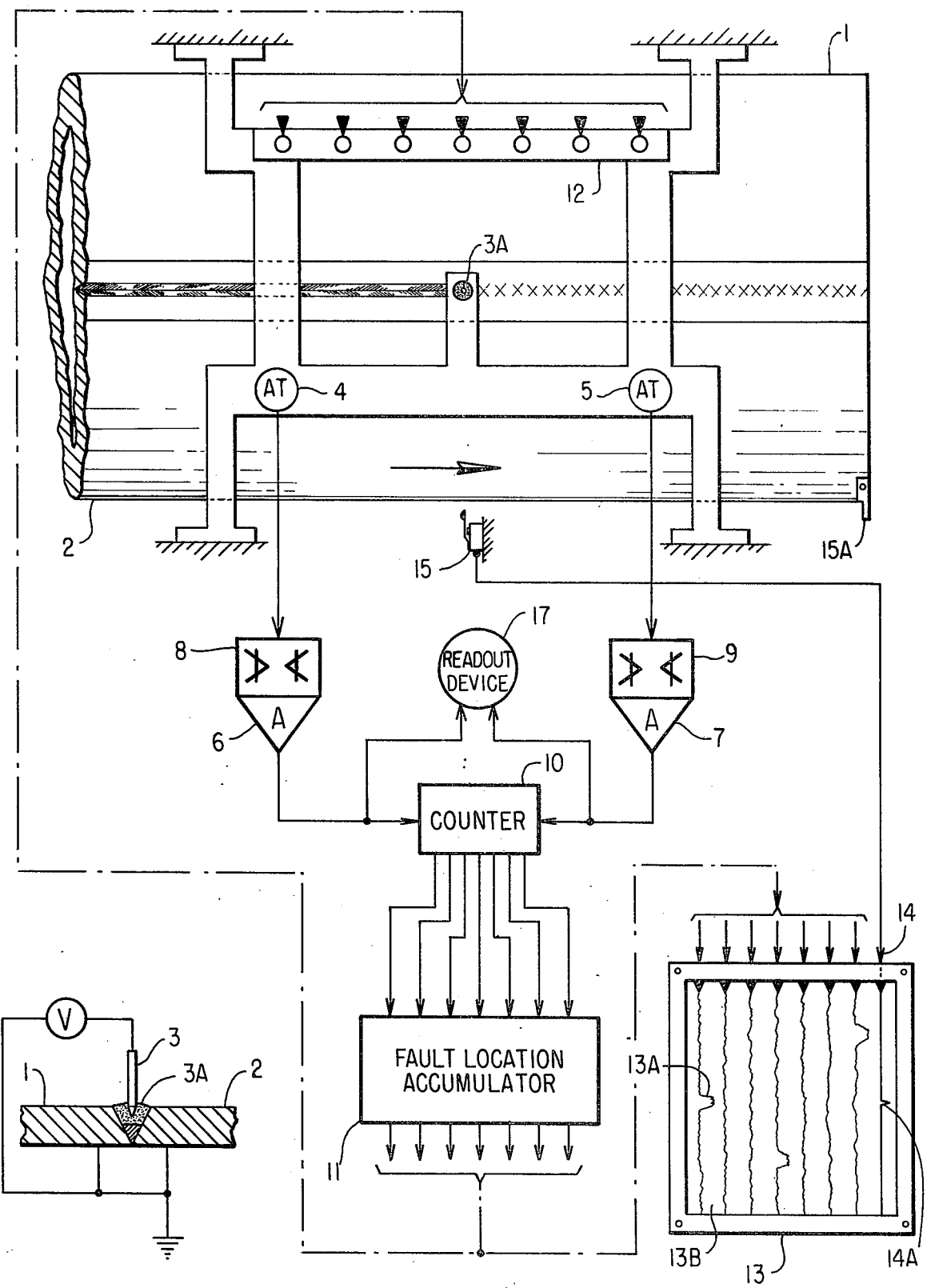
FIG. 1 is a schmematic diagram of a weld monitor embodying the principles of this invention.
FIG. 2 is a fragmentary side elevation view showing in elementary form a typical submerged arc welder.

Referring to the drawings there is shown a weld monitor applied to the in-situ detection and location of flaws in a weld joining workpieces 1 and 2. Such workpieces may be of any configuration such as flat, curved or circular. In some cases the welder has an electrode 3 which is moved while the workpieces to be joined are held stationary. In the case shown, the electrode 3 is held stationary and the workpieces 1 and 2, such as sections of heavy walled pipe, are moved in the direction of the arrow at a selected speed past the electrode. In either case typical movement of the workpieces relative to the electrode may be taken as being in the order of twelve inches per minute. As shown in FIG. 2 the arc produced at the electrode 3 is submerged throughout the welding operation in a flux 3A.

In present day practice the integrity of the weld is determined only after the weld is completed and the joined workpieces move to a test station by nondestructive methods such as ultrasonic or radiography. If a flaw is detected, it is necessary to remove a substantial section of the weld to expose the flaw. As upwards of seventy five or more passes may be required to complete a weld this operation coupled with the necessity to reweld the entire section of the weld removed is extremely costly and time consuming.

In accordance with this invention flaws are detected and located immediately upon formation so that the welding operation may be then and there interrupted, the defective segment of the weld removed, repairs made and the welding process continued, thus materially reducing lost time and expense.

Referring to the drawings, acoustic emissions traveling through one or the other of the workpieces, such as the workpiece 2, are sensed by a leading transducer 4 and a following transducer 5 which may be of any suitable type such as the piezoelectric or electromagnetic types. The transducers 4 and 5 are maintained in fixed positions relative to the electrode 3 and adjacent to and on a line running parallel with the weld cavity. By a leading transducer is meant one which is located ahead of the electrode 3 immediately before fusion occurs. By a following transducer is meant one which is located after the electrode 3 and immediately following the solidification zone. Ordinarily it is while in the solidification zone that a flaw, such as entrapped slag, generates an acoustic emission. It is to be recognized, however, that under certain conditions, perhaps governed by material thickness and welding conditions, a previously formed flaw will generate an acoustic emission in subsequent passes when approaching the high temperature zone surrounding the arc.

The transducers 4 and 5, while sensing fault acoustic emissions, also sense miscellaneous acoustic emissions traveling through the work pieces and which are collectively referred to as background noise. Fault acoustic emissions peak within an ascertainable range of frequencies. Further, the average background noise is of relatively small amplitude. Accordingly such background noise as sensed by the transducers 4 and 5 can be substantially eliminated by incorporating in amplifiers 6 and 7, receiving the signals generated in transducers 4 and 5 respectively, band pass filters as shown at 8 and 9 which allow only acoustic emissions having an amplitude above a predetermined threshold value to pass, and passing only that band of frequencies which includes those generated by a fault. Thus there is available at the outputs of band pass filters 8 and 9 signals having an amplitude greater than a predetermined threshold value and falling within a predetermined band of frequencies and hence indicative of a fault.

To determine the location of a detected fault the output signals from amplifiers 6 and 7 input to a counter 10. The counter 10 is turned on when it receives a signal from one amplifier and turned off when it receives a signal from the other amplifier and simultaneously generates an output signal which is transmitted to an accumulator 11. The counter counts up or down from an intial setting depending upon whether started by a signal from amplifier 6 or from amplifier 7. A zero time of arrival difference is considered false and no output signal is generated as acoustic emissions arriving simultaneously at transducers 4 and 5 are typical of background noise arriving from locations other than the weld zone. Counts below a predetermined minimum and above a predetermined maximum are also rejected as originating from a source outside the monitoring region lying between transducers 4 and 5, or that an acoustic emission was received by one transducer and not the other. After completion of each operation the counter 10 resets to the initial setting.

It will therefore be recognized that operation by spurious signals is substantially eliminated by requiring that the signal source must originate between detectors 4 and 5, must be received by both detectors, have a frequency within the predetermined band of frequencies, and have an amplitude above a preset threshold value. To further avoid operation by spurious signals the invention provides that a plurality of valid signals must be received from within preselected segments of the weld bead lying between transducers 4 and 5. By way of illustration, the monitoring region lying between transducers 4 and 5 is shown as divided into seven segments. It will be evident that this region may be divided into more or fewer segments of equal or unequal lengths depending upon the exigencies of a particular application. Fault locations established by the counter 10 lying within each selected segment are transmitted to a location accumulator 11, which upon there being a preselected number of fault signals received from within a given segment, triggers a fault location marker 12 to mark on the work piece 1, the segment in which the selected number of fault signals originated. Simultaneously the output signal may be transmitted to an alarm and location readout device as shown at 13.

Such a device may take a variety of forms for exhibiting the fault location. For purposes of illustration, the device 13 is shown as a strip chart recorder provided with a recording element for each of the segments 1 – 7. Under normal operation the traces produced by such elements on the cooperating moving strip chart 13B are more or less undulating lines. As shown at 13A, however, pronounced trace marks are generated upon the receipt of a signal from the accumulator 11.

Also included in the recorder 13 is a weld pass marker 14, which produces a mark as shown at 14A at the start of each weld pass. The marker 14 is energized at the start of each pass by a switch 15, momentarily closed by a trigger 15A removably secured to the work piece 2. Through correlation of the chart 13B ordinates with the length of the weld segments, heretofore described, and the correlation of the chart 13B abscissae with the displacement of the work pieces 1 and 2 relative to the electrode 3, the surface location of a fault on the weld bead may be determined from the chart location of a mark, such as shown at 13A. The depth of a fault from the surface of the work pieces may be determined by counting, by means of recorder 14, the number of weld passes from the first or root pass, inasmuch as each pass lays up substantially the same amount of weld bead.

A readout device 17, such as a CRT display, may be provided to exhibit the reception by transducers 4 and 5 of acoustic emissions falling within the predetermined band of frequencies and having an amplitude above the predetermined threshold value.

Conventional circuit components as may be required, such as pre-amplifiers, shielding, grounding and the like, have been omitted from the drawings and description as it is evident that such components may be included where and when required.

I claim:

1. A system for the in-situ detection and location of flaws in welds wherein a work piece is moved relative to a welder electrode, the combination comprising, a first acoustic transducer located a first preselected distance ahead of the electrode, a second acoustic transducer located a second preselected distance following the electrode, said first and second transducers each receiving the acoustic emissions generated by a fault within the weld bead and generating an output signal corresponding in amplitude and frequency to the amplitude and frequency of said acoustic emissions, and means responsive to the output signals of said transducers generating a signal indicative of the location of the fault in said bead comprising means determining the difference in the times required for emissions from said fault to travel to said first and second transducers.

2. The combination as set forth in claim 1 further including means accumulating the signals indicative of the location of a fault and generating an output signal upon the accumulation of a predetermined number of fault signals originating within a predetermined segment of the weld bead.

3. The combination as set forth in claim 2 further including means responsive to the output signal of said accumulating means marking the segment of the weld bead on the work piece in which the predetermined number of fault signals originated.

4. The combination as set forth in claim 2 further including means responsive to the output signal of said accumulating means exhibiting the segment of the weld bead in which the predetermined number of fault signals originated.

5. The combination as set forth in claim 4 wherein exhibiting means includes a marking means responsive to said output signal and a cooperating chart driven at a speed in predetermined ratio to the speed of the work piece relative to the electrode.

6. The combination as set forth in claim 1 wherein said means generating a signal indicative of the location of the fault in said bead comprises a counter turned on when receiving the first to arrive signal from one transducer and turned off and simultaneously generating an output signal when the second to arrive signal is received from the other transducer.

7. The combination as set forth in claim 1 wherein a plurality of passes of the electrode relative to the work piece are required to complete the weld, further including means exhibiting each weld pass whereby the pass in which a fault occurred may be determined.

* * * * *